United States Patent [19]

Akiyama et al.

[11] 4,215,689

[45] Aug. 5, 1980

[54] INJECTING APPARATUS FOR MEDICAL LIQUID

[75] Inventors: Taichiro Akiyama; Fumiyo Mutou, both of Tokyo, Japan

[73] Assignee: Koken Co., Ltd., Tokyo, Japan

[21] Appl. No.: 924,954

[22] Filed: Jul. 17, 1978

[30] Foreign Application Priority Data

Jul. 27, 1977 [JP] Japan ................................ 52-89978
Dec. 12, 1977 [JP] Japan ................................ 52-149098

[51] Int. Cl.² .................... F04B 17/04; F04B 45/08; A61M 5/00; A41D 1/04
[52] U.S. Cl. ............................. 128/214 F; 128/213 R; 128/214 R; 128/DIG. 12; 417/234; 417/478; 3/1.7
[58] Field of Search .................. 128/214 F, DIG. 12, 128/214 R, 213; 417/234, 478; 222/214

[56] References Cited

U.S. PATENT DOCUMENTS

| | | | |
|---|---|---|---|
| 2,772,817 | 12/1956 | Jauch | 417/478 X |
| 2,915,222 | 12/1959 | Purinton | 222/214 X |
| 3,349,716 | 10/1967 | Weber | 417/478 |
| 3,359,910 | 12/1967 | Latham, Jr. | 417/478 X |
| 3,366,060 | 1/1968 | Jennings | 417/234 |
| 3,496,878 | 2/1970 | Hargest et al. | 128/214 F |
| 3,518,033 | 6/1970 | Anderson | 417/478 |
| 3,731,322 | 5/1973 | Kresse | 3/1.7 |
| 3,839,983 | 10/1974 | McAusland | 417/478 X |
| 4,087,864 | 5/1978 | LaBove et al. | 128/214 R X |

*Primary Examiner*—Henry K. Artis
*Attorney, Agent, or Firm*—McDougall, Hersh & Scott

[57] ABSTRACT

Injecting apparatus comprises means to hold the apparatus against a living body, and a medical liquid in a reservoir of the apparatus is pumped by a pump means which is driven by movement of some portion of the living body, so as to be injected into the living body. The medical liquid may be injected little by little, in which case each cycle of the pump means is effected by a plurality of movements of the living body. The reservoir is made of resilient material, for example, silicone rubber. A modified reservoir comprises an inner bag and an outer bag, with an intermediate space therebetween, which may be filled with a physiological solution of sodium chloride.

11 Claims, 15 Drawing Figures

INJECTING APPARATUS FOR MEDICAL LIQUID

BACKGROUND OF THE INVENTION

1. Field of the Invention

This invention relates to an injecting apparatus for medical liquid, and more specially, is directed to an apparatus suitable for injecting medical liquid into a living body little by little.

2. Description of the Prior Art

For injecting medical liquid into a human body little by little, a drip feed apparatus is commonly used. This requires that the patient lies on a bed, and medical liquid, which may be a liquid medicine, is drip fed into the patient's body by the apparatus. The patient cannot move freely, and the process may well be painful. Moreover, the apparatus lacks mobility, and also it is rather difficult to control the quantity of liquid injected.

SUMMARY OF THE INVENTION

One object of this invention is to provide an injecting apparatus which can be used when a patient is in any posture.

Another object of this invention is to provide an injecting apparatus which does not cause pain to a patient.

A further object of this invention is to provide an injecting apparatus which injects a medical liquid into living body in accordance with the metabolism of the living body.

A still further object of this invention is to provide an injecting apparatus, a pump means of which is driven by movement of some part of a living body.

A still further object of this invention is to provide an injecting apparatus which injects a medical liquid little by little into a living body.

According to the present invention there is provided an injecting apparatus for medical liquid, the apparatus comprising:
 means to hold the apparatus against a living body;
 a reservoir for storing said medical liquid;
 a pump means to pump said medical liquid; and
 means to derive from a movement of said living body energy for driving said pump means;
whereby said medical liquid is injected into said living body by said pump means, when the apparatus is held against said living body and said pump means is driven by said movement.

The above, and other objects, features and advantages of this invention will be apparent from the following detailed description of illustrative embodiments thereof which is to be read in connection with the accompanying drawings.

DESCRIPTION OF THE PREFERRED EMBODIMENT

Figure 1:
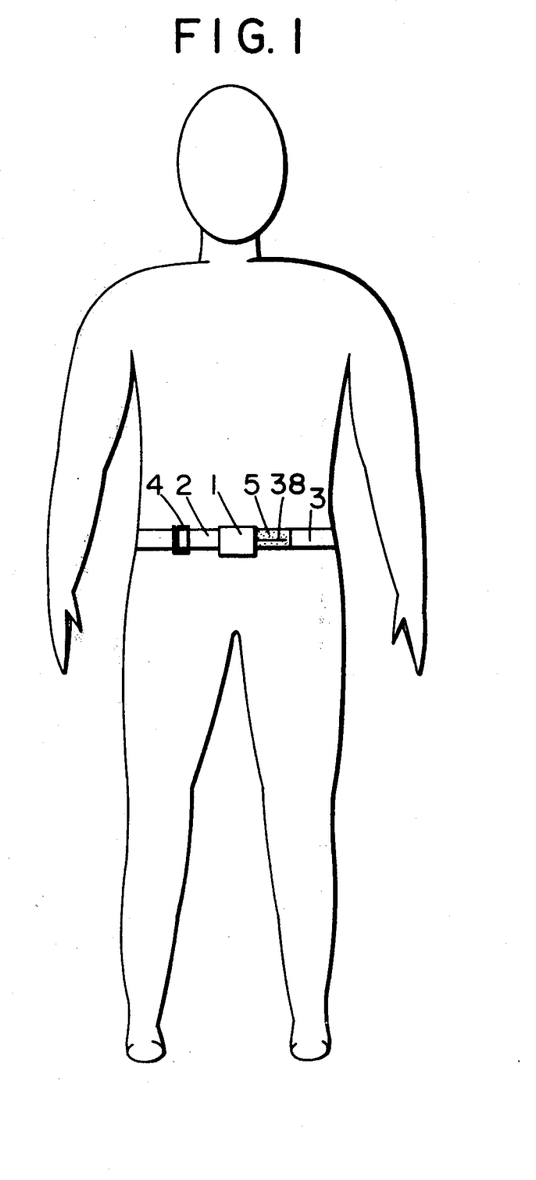
FIG. 1 is a front view of a human body equipped with an embodiment of injecting apparatus according to the invention for injecting an anti-tumour agent.
Figure 2:
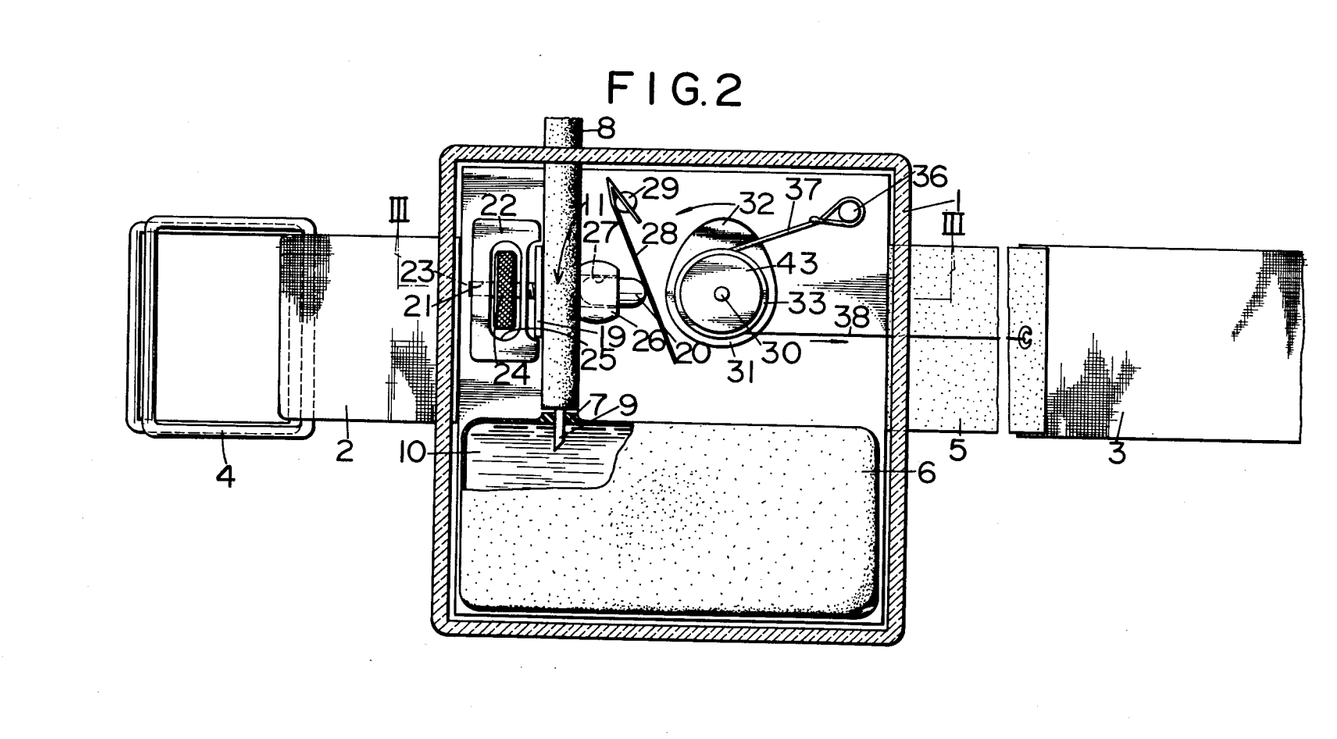
FIG. 2 is an enlarged plan view of the injecting apparatus, a cover of which is removable.

The injecting apparatus to be described with reference to the drawings comprises a case 1 to respective ends of which are coupled a pair of belts 2 and 3 as shown in FIG. 1. By means of the belts 2 and 3, the apparatus is held against some portion of a human body, for example on the abdomen of a patient. A catch 4 is fixed to the free end of the belt 2, as shown in FIG. 2. By means of the catch 4, the free end of the belt 2 is connected to the free end of the other belt 3. The belt 2 is directly connected to the case 1, but the belt 3 is, in fact, connected to the case 1 by a stretchy rubber belt 5 which expands and contracts as the patient breathes.

Figure 3:
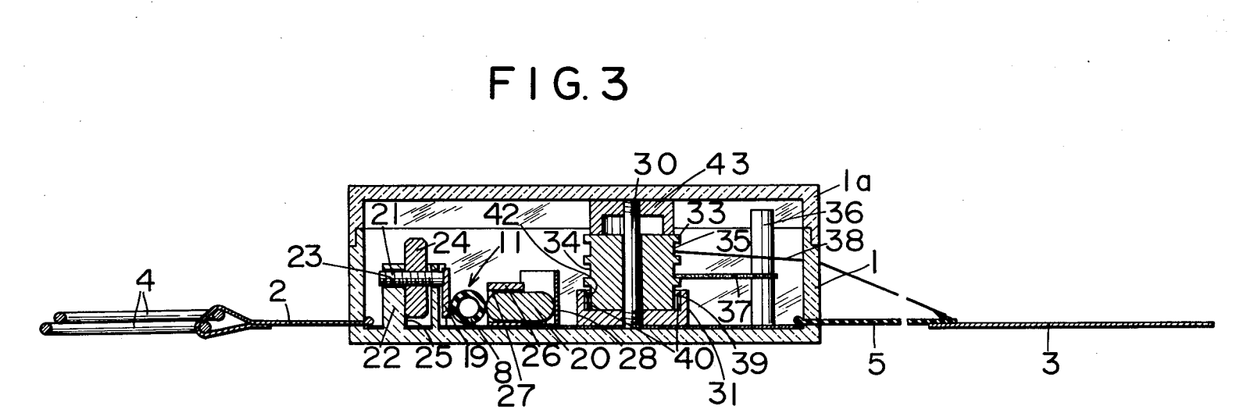
FIG. 3 is a cross sectional view along the line III—III in FIG. 2.

The case 1 is made of transparent synthetic resin, and is provided with a removable cover 1a (FIG. 3). FIG. 2 shows the inside of the case 1. A reservoir in the form of a bag or tank 6 is disposed in the case 1, and is made of resilient material, such as silicone rubber. A medical liquid 10, such as an anti-tumour agent is stored in the bag 6. A thickened portion 7 is formed on the side wall of the bag 6. A needle 9 penetrates the thickened portion 7, and the needle 9 is connected to an end of a conduit 8, so that the medical liquid 10 is led into the conduit 8 from the bag 6 through the needle 9.

Figure 7A:
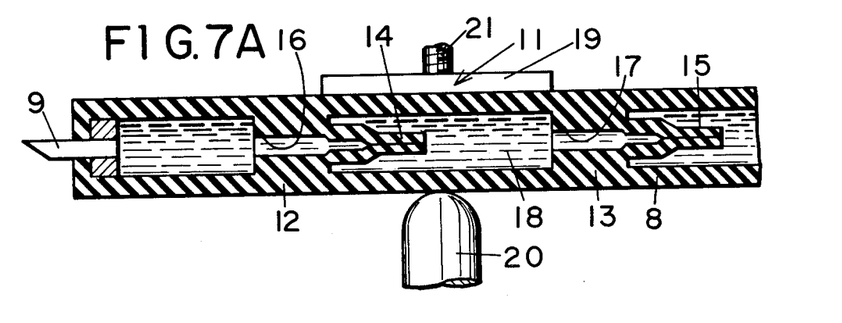
FIG. 7A is a cross sectional view of a conduit wherein a pump means is arranged.

The conduit 8 is provided with a pump 11 as shown in FIG. 7A. The pump 11 comprises a pair of separating walls 12 and 13 formed in the conduit 8. The separating walls 12 and 13 define respective small apertures 16 and 17 having valve means 14 and 15 respectively. Thus a pump chamber 18 is formed in the conduit 8 between the walls 12 and 13, and the medical liquid 10 is pumped out by the deformation of the conduit 8 in the radial direction.

The conduit 8 and the pump 11 are made of resilient material, for example silicone rubber, and the pump 11 is arranged between a receiving plate 19 and a push rod 20 which are positioned in the case 1. A bolt 21 is fixed to the receiving plate 19 and penetrates rotatably through a hole 23 formed on a supporting member 22 as shown in FIG. 3. The supporting member 22 is integral with the case 1. The bolt 21 is screwed into an adjusting nut 24. The nut 24 is received in a recess 25 of the supporting member 22. Hence, by rotating the nut 24, the receiving plate 19 moves in the radial direction of the conduit 8 or to the left or right in FIGS. 2 and 3. Thereby the quantity of the liquid pumped by a stroke of the pump 11 varies. The push rod 20 is slidably supported by the guide hole 27 of the guide member 26, and is movable in the radial direction of the conduit 8, or to the left or right in FIGS. 2 and 3. One end of the push rod 20 contacts the peripheral surface of the conduit 8 in the region of the pump 11. The other end of the push rod 20 contacts a leaf spring 28, one end of which is bent over and supported by a pin 29 mounted on the case 1.

Figure 4:
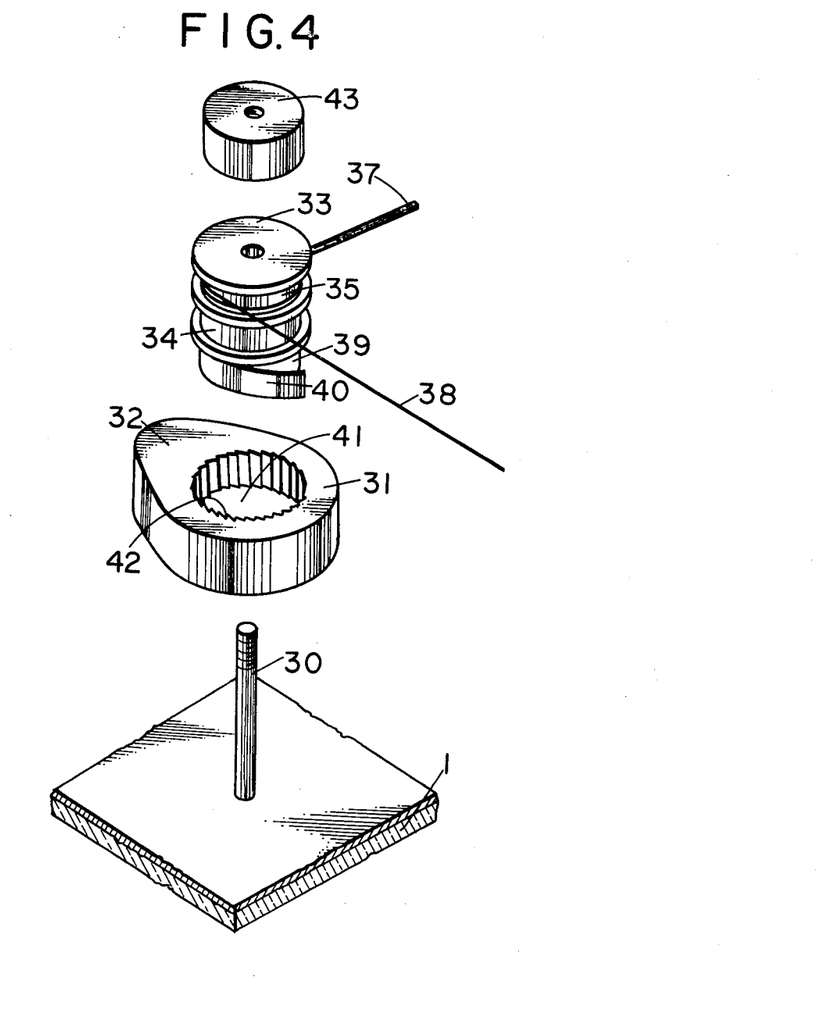
FIG. 4 is an exploded perspective view of a driving assembly for a pump means of the apparatus.

The leaf spring 28 deforms elastically, when a cam 31 rotates around a supporting shaft 30, and an actuating portion 32 pushes the leaf spring 28. A pulley 33 is also supported by the supporting shaft 30. A pair of grooves 34 and 35 are defined in the peripheral surface of the pulley 33 as shown in FIG. 4. An elastic string 37 is wound in the first groove 34. One end of the elastic string 37 is fixed to the case 1 by a pin 36, and other end of the elastic string 37 is fixed to the pulley 33. An inelastic string 38 is wound in the second groove 35. One end of the inelastic string 38 is fixed to the rubber belt 5 near the connecting point of the rubber belt 5 and the belt 3, and other end of the inelastic string 38 is fixed to the pulley 33. A pair of leaf springs 40 are fixed to a peripheral surface of a boss 39 of the pulley 33. The free ends of the leaf springs 40 extend tangentially to the pulley 33. The boss 39 of the pulley 33 and the pair of leaf springs 40 are received in a circular recess 41 in the cam 31. Ratchet teeth 42 are formed on the inner surface of the recess 41. The leaf springs 40 and the ratchet teeth 42 constitute a one-way clutch. Therefore couter-clockwise rotation of the pulley 33 as seen in FIG. 2 is transmitted to the cam 31, and clockwise rotation of the pulley 33 as seen in FIG. 2 is not transmitted to the cam 31. A stop ring 43 is fixed at the top of the shaft 30. The pulley 33 is prevented from dropping off the shaft 30 by the stop ring 43.

The operation will now be described.

Figure 5A:
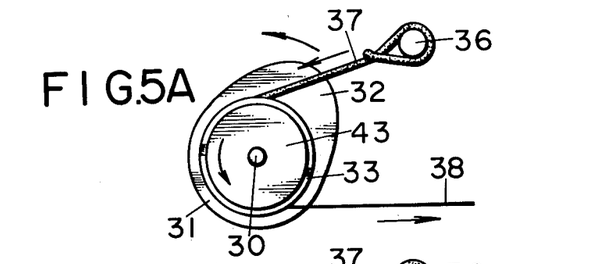
FIG. 5A is a plan view of the driving assembly when a cam is driven by a pulley on inspiration during breathing by the human body.

The apparatus is held against, for example, the abdomen of a patient by the pair of belts 2 and 3. The abdomen expands and contracts alternately, in accordance with inspiration and expiration in breathing, so that the circumference of the abdomen varies. As the belts 2 and 3 are inelastic, the rubber belt 5 expands and contracts with the breathing. The inelastic string 38 is tensioned by the expansion of the rubber belt 5, when the abdomen expands with the inspiration, because one end of the inelastic string 38 is fixed to the rubber belt 5 near the connecting point of the rubber belt 5 and the belt 3. The pulley 33 rotates counter-clockwise for example by 30° around the supporting shaft 30 in FIG. 5A when the string 38 is tensioned by the rubber belt 5, because the string 38 is wound in the second groove 35 of the pulley 33. At the same time, the elastic string 37 is stretched, and the string 37 is charged with elastic energy to rotates the pulley 33 in the clockwise direction, because the elastic string 37 is wound in the first groove 34. The counter-clockwise rotation of the pulley 33 is transmitted to the cam 31 through the leaf springs 40 and the ratchet teeth 42, and the cam 31 rotates counter-clockwise in FIG. 5A around the shaft 30, for example, by 30°.

Figure 5B:
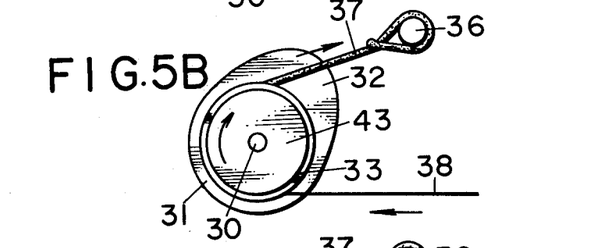
FIG. 5B is a plan view of the driving assembly when the pulley rotates in the reverse direction on expiration during breathing by the human body.

The abdomen contracts by the expiration in breathing, and hence the rubber belt 5 contracts. Then the string 38 is released from the tensioned state. The pulley 33 rotates clockwise in FIG. 5B around the shaft 30 due to the stretched elastic string 37. The clockwise rotation of the pulley 33 is not transmitted to the cam 31, because the leaf springs 40 do not engage with the ratchet teeth 42, but the free ends of the leaf springs 40 slip on the ratchet teeth 42 due to elastic deformation of the leaf springs 40. Thus, the cam 31 does not rotate at this stage.

Figure 5C:
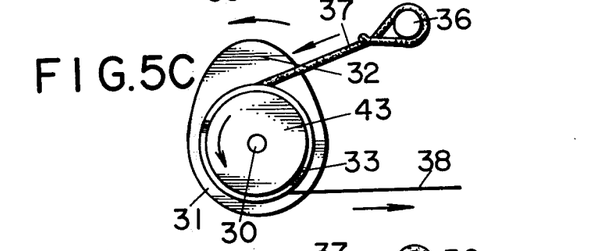
FIG. 5C is a plan view of the driving assembly when the cam is further driven by the pulley on a latter inspiration.
Figure 5D:
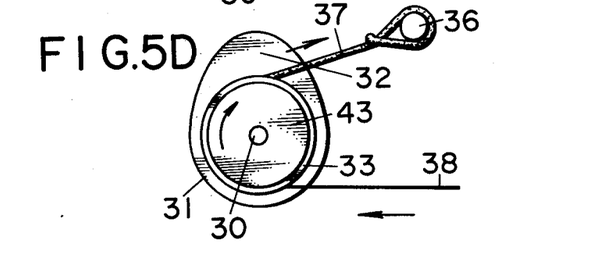
FIG. 5D is a plan view of the driving assembly when the pulley again rotates in the reverse direction on a later expiration.

The next expansion of the abdomen by inspiration tensions the string 38, and the pulley 33 rotates counter-clockwise in FIG. 5C by 30°. This rotation of the pulley 33 is transmitted to the cam 31, and the cam 31 rotates counter-clockwise by a further 30°. Next, the abdomen contracts and the pulley 33 rotates clockwise, as shown in FIG. 5D.

Figure 6:
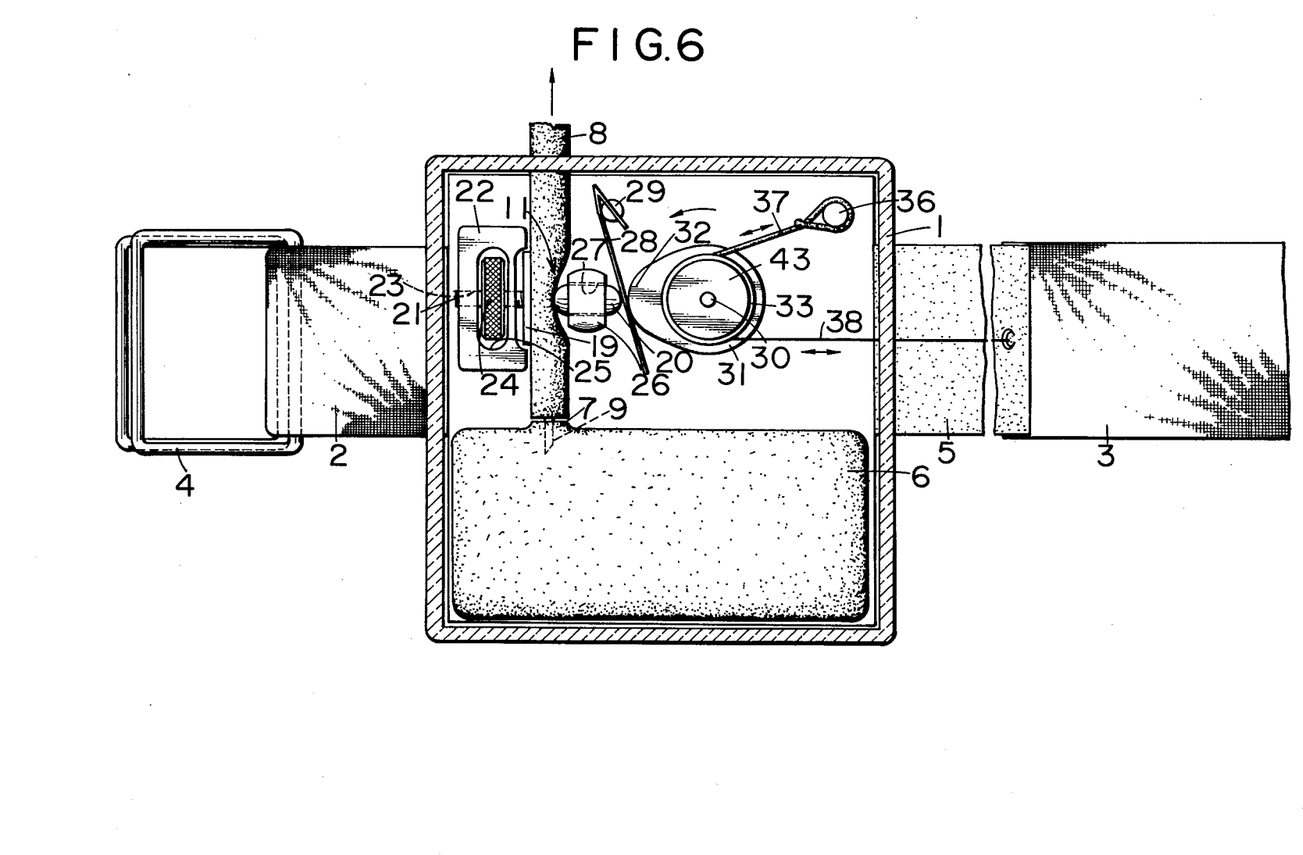
FIG. 6 is a plan view of the injecting apparatus when a pump means is driven by the cam and the anti-tumour agent is injected.

As described above, the cam 31 is rotationally driven intermittently, for example by 30°, by movement resulting from the patient's breathing, and then the actuating portion 32 of the cam 31 contacts with the leaf spring 28 as shown in FIG. 6. Hence the leaf spring 28 deforms elastically, and pushes the push rod 20. Therefore, the push rod 20 displaces to the left in FIG. 6 along the guide hole 27, and the free end of the rod 20 pushes the side wall of the conduit 8 in the region of the pump 11.

Figure 7B:
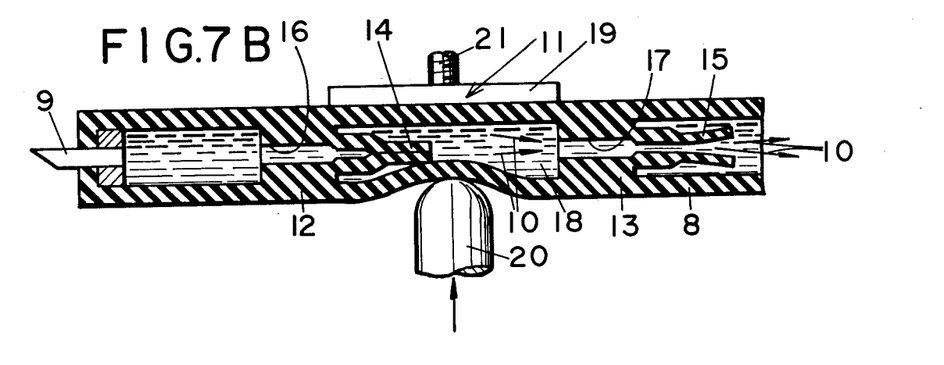
FIG. 7B is a cross sectional view of the conduit when the anti-tumour agent is pumped by the pump means.

Thus the side wall of the conduit 8 deforms elastically as shown in FIG. 7B, and the pressure of the medical liquid 10 in the pump chamber 18 rises, when the conduit 8 is pushed by the push rod 20. Hence, the medical liquid 10 flows out of the pump chamber 18 through the small aperture 17, because the valve means 15 is opened by the increased pressure. At this stage, the valve means 14 is closed, and reverse flow of the medical liquid 10 into the bag 6 does not occur. As the conduit 8 is provided with a needle (not shown) at the free end, and as the needle is pierced into an artery or vein of the abdomen, the medical liquid 10 pumped through the conduit 8 is injected into the artery or vein. One pumping stroke may, for example, be accomplished by twelve breaths, when the cam 31 rotates 30° for each breath. Accordingly a very small quantity of medical liquid 10 such as anti-tumour agent may be injected into the patient. For instance 5 mml of anti-tumour agent may be injected into the patient per 24 hours.

Figure 7C:
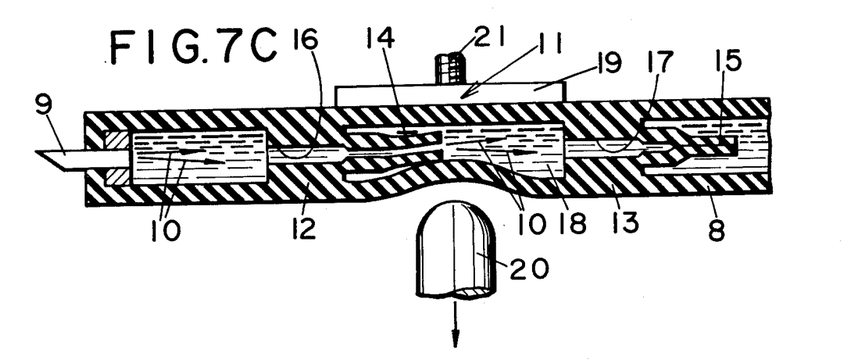
FIG. 7C is a cross sectional view of the conduit when a push rod moves backward and further anti-tumour agent is led into the conduit.

When the cam 31 rotates further due to the breathing, the actuating portion 32 of the cam 31 separates from the leaf spring 28, and the push rod 20 is released from the pushing forces. Then the side wall of the conduit 8 is restored to the original state by the resiliency thereof. Therefore the pressure of the medical liquid 10 in the pump chamber 18 drops suddenly. Hence more medical liquid 10 is fed into the pump chamber 18 through the small aperture 16 and the valve means 14, as shown in FIG. 7C. At this stage, the medical liquid 10 is prevented from flowing backward because the valve means 15 is closed. This further medical liquid 10 is pumped by the forward movement of the push rod 20, and injected into the patient.

As described above, the anti-tumour agent is injected into the patient little by little by the breathing.

Figure 8:
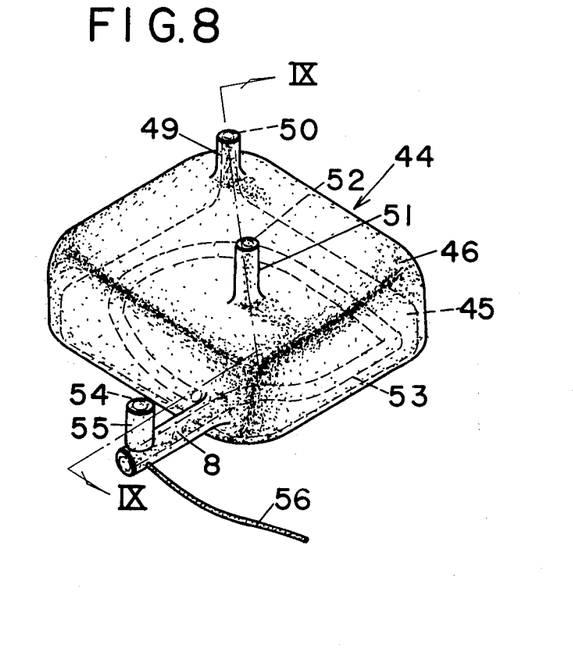
FIG. 8 is a perspective view of a modified reservoir for medical liquid.
Figure 9:
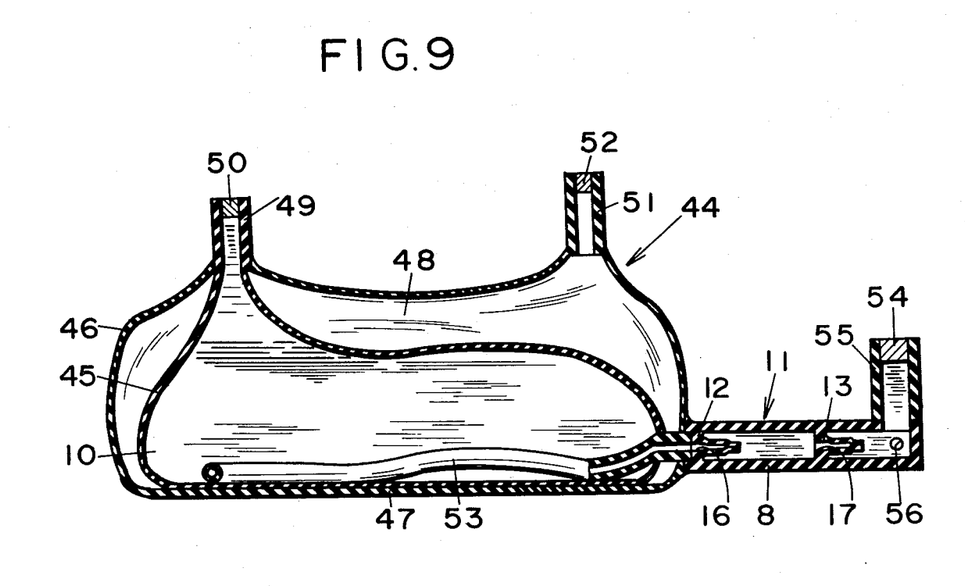
FIG. 9 is a cross sectional view along the line IX—IX in FIG. 8.
Figure 10:
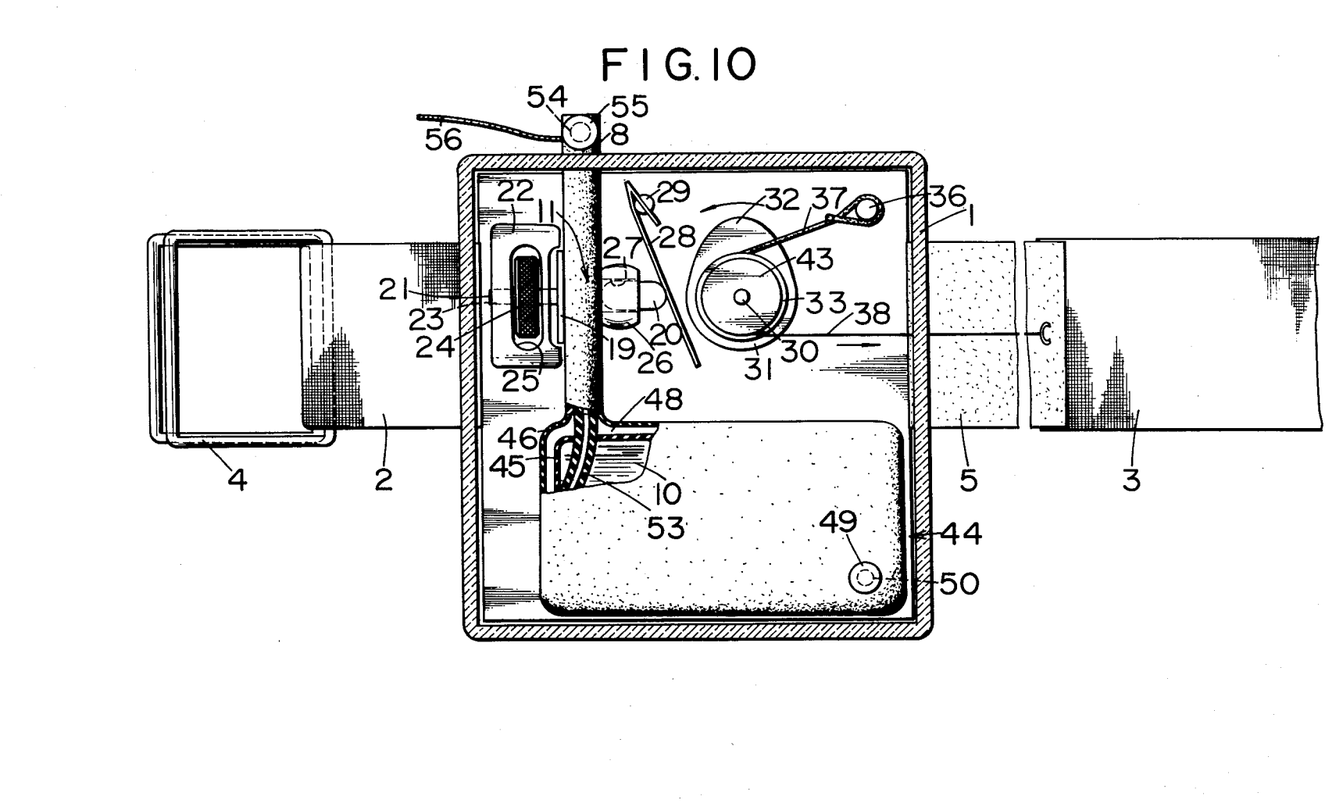
FIG. 10 is a plan view of the injecting apparatus provided with the modified reservoir.

Next, a modified form of the bag or tank for the medical liquid will be described with reference to FIGS. 8 to 10.

The modified tank 44 comprises an inner bag 45 and an outer bag 46, both made of resilient material, for example, silicone rubber. The inner bag 45 is positioned inside the outer bag 46. A thickened bottom wall 47 of the outer bag 46 is of a thickness such that air or other gas is prevented from passing through the bottom wall 47. A bottom wall of the inner bag 45 adheres closely to the bottom wall 47 of the outer bag 46. The side and upper walls of the inner bag 45 are separated from the corresponding portions of the outer bag 46, and an intermediate space 48 is formed between the inner bag 45 and the outer bag 46. The inner bag 45 is provided with a conduit 49 which projects out of the outer bag 46. A thickened portion 50 is formed at the top of the conduit 49. A needle of a syringe pierces through the thickened portion 50 and the medical liquid 10 is injected into the inner bag 45. The outer bag 46 is provided with a conduit 51, and a thickened portion 52 is formed at the top of the conduit 51. A needle or syringe pierces through the thickened portion 52 and a physiological solution of sodium chloride is injected into the intermediate space 48 or air in the intermediate space 48 is removed from the bag 46. A tail pipe 53 is arranged inside the inner bag 45. One end of the tail pipe 53 opens in the bag 45, and other end of the tail pipe 53 passes through the side walls of the inner bag 45 and outer bag 46 and is connected to the conduit 8. Accordingly, the medical liquid 10 in the inner bag 45 is led to the conduit 8 through the tail pipe 53. A branch pipe 55 is formed at the free end of the conduit 8, and a thickened portion 54 is formed at the free end of the branch pipe 55. A needle of a syringe pierces through the thickened portion 54, and another kind of medical liquid, for example a heart medicine is injected into the conduit 8. In this way the anti-tumour agent and the heart medicine are mixed and injected into the human body.

With the modified tank 44, air or other gas is prevented from entering the inner bag 45, and is prevented from being injected into the patient with the medical liquid. Thus in the bottom portion, the air is prevented from entering the bags 45 and 46 by the thickened bottom wall 47, and in the side and upper portions, air is prevented from entering the inner bag 45 by the physiological solution of sodium chloride in the intermediate space 48. The inner bag 45 becomes flat and the medical liquid 10 in the bag 45 is smoothly fed from the bag 45 because the resiliency of the inner bag 45 and the outer bag 46 cause them to contract, and because the bottom portion of the bag 46, which consists of the thickened wall 47, does not contract.

The conduit 8 is provided with a pump 11 comprising a pair of separating walls 12 and 13. The walls 12 and 13 define respective small apertures 16 and 17, provided with respective valve means as shown in FIG. 9. The pump 11 is arranged between the receiving plate 19 and the push rod 20 in the case 1 as shown in FIG. 10. The pumped medical liquid 10 is injected into the patient through the injecting pipe 56 and a needle (not shown) connected to the free end of the pipe 56. Other parts in FIG. 10 which correspond to those in FIG. 2 are denoted by the same reference numerals, and the description thereof will be omitted.

Although an illustrative embodiment of this invention has been described in detail herein with reference to the accompanying drawings, it is to be understood that the invention is not limited to this precise embodiment or the described modification, and that various changes and further modifications may be made therein by one skilled in the art without departing from the scope or spirit of the invention as defined in the appended claims.

For example, the pump may alternatively be driven by some movement of the living body other than breathing.

Moreover, the injecting apparatus may be used for injecting other kinds of medical fluid. The quantity injected per unit time may also be changed in accordance with the purpose or the nature of the medicine.

What is claimed is:

1. In an apparatus for injecting liquid into the body including means supporting the apparatus on the torso, a pump, a liquid reservoir connected to the pump, and a conduit connected to the pump and entering into the body for conveying the liquid into the body, the improvement in actuating means for said pump comprising a pump operating member, and drive means connected to said operating member for driving said operating member, said drive means including means movable in response to breathing movement, and said drive means further including indexing means moving the drive means an increment in response to each breathing movement, a plurality of increments of movement resulting in a single pumping operation whereby liquid injection occurs at a frequency less than the breathing frequency.

2. An injecting apparatus according to claim 1, wherein said reservoir is made of resilient silicone rubber.

3. An injecting apparatus according to claim 1, wherein said conduit is formed integrally with said reservoir.

4. An injecting apparatus according to claim 2, wherein said reservoir comprises an inner bag and an outer bag, and an intermediate space is formed between said inner bag and said outer bag, said intermediate space being filled with a physiological solution of sodium chloride.

5. An apparatus according to claim 1 wherein said means supporting the apparatus comprises belt means including an elastic belt portion which expands and contracts alternately in accordance with the breathing movement, said pump being driven in response to the expansion and contraction of said elastic belt portion.

6. An apparatus according to claim 5 wherein said drive means comprises a rotor which rotates forward and backward in accordance with the expansion and contraction of said elastic belt portion, a cam having a actuating portion, and a one-way clutch means arranged between said rotor and said cam, said pump being driven by said actuating portion of said cam as said cam rotates to provide said increments of movement.

7. An apparatus according to claim 6 wherein said one-way clutch means comprises at least one leaf spring fixed to said rotor with the free end of said leaf spring extending in the tangential direction of said rotor, and ratchet teeth defined on the inner surface of a circular recess formed on said cam for engagement with said leaf spring.

8. An injecting apparatus according to claim 7 wherein said cam rotates to provide an increment of movement of about 30° in response to one expansion of said elastic belt portion, whereby one cycle of said pump means is effected by about twelve breathing movements.

9. An apparatus according to claim 1 wherein said pump comprises a resilient conduit having a pair of separating walls with respective small apertures, said pair of walls forming a pump chamber and said small apertures being provided with respective valve means.

10. An apparatus according to claim 9 wherein said conduit is pinched between a receiving plate and a push member pushed by said actuating portion of a driving cam, and wherein said receiving plate is movable to adjust said pump chamber.

11. An apparatus according to claim 1 wherein said conduit is provided with a branch pipe whereby a second liquid can be mixed and injected into said living body along with said first-mentioned liquid.

* * * * *